(12) United States Patent
Stopek (10) Patent No.: US 9,662,018 B2
(45) Date of Patent: May 30, 2017

(54) INTEGRATED SELF-FIXATING VISUALIZATION DEVICES, SYSTEMS AND METHODS

(71) Applicant: Covidien LP, Mansfield, MA (US)

(72) Inventor: Joshua Stopek, St. Louis Park, MN (US)

(73) Assignee: Covidien LP, Mansfield, MA (US)

( * ) Notice: Subject to any disclaimer, the term of this patent is extended or adjusted under 35 U.S.C. 154(b) by 181 days.

(21) Appl. No.: 13/790,056

(22) Filed: Mar. 8, 2013

(65) Prior Publication Data

US 2013/0261469 A1    Oct. 3, 2013

Related U.S. Application Data

(60) Provisional application No. 61/617,830, filed on Mar. 30, 2012.

(51) Int. Cl.
| | | |
|---|---|---|
| *A61B 5/00* | (2006.01) | |
| *A61F 2/00* | (2006.01) | |
| *A61B 17/00* | (2006.01) | |
| *A61B 90/30* | (2016.01) | |
| *A61B 90/00* | (2016.01) | |

(52) U.S. Cl.
CPC .......... *A61B 5/0077* (2013.01); *A61B 90/361* (2016.02); *A61B 90/37* (2016.02); *A61F 2/0063* (2013.01); *A61B 90/30* (2016.02); *A61B 2017/00004* (2013.01); *A61B 2017/00221* (2013.01); *A61B 2090/309* (2016.02); *A61B 2090/364* (2016.02)

(58) Field of Classification Search
CPC .............. A61B 19/5212; A61B 5/6882; A61B 2019/5227; A61B 1/041; A61B 5/0077; A61B 90/37; A61B 90/361; A61B 2090/309; A61B 2090/364; A61B 90/30; A61B 2017/00004; A61B 2017/00221; A61F 2/0063
See application file for complete search history.

(56) References Cited

U.S. PATENT DOCUMENTS

| | | |
|---|---|---|
| 6,545,702 B1 | 4/2003 | Konolige et al. |
| 7,239,345 B1 | 7/2007 | Rogina |
| 7,559,887 B2 | 7/2009 | Dannan |
| 7,646,544 B2 | 1/2010 | Batchko et al. |

(Continued)

FOREIGN PATENT DOCUMENTS

| | | |
|---|---|---|
| CN | 101612030 | 12/2009 |
| DE | 202006011532 | 12/2006 |

(Continued)

OTHER PUBLICATIONS

U.S. Appl. No. 13/444,908, filed Apr. 12, 2012, Inventor Joshua Stopek.

(Continued)

*Primary Examiner* — Katherine Fernandez
*Assistant Examiner* — Angela M Hoffa (57) ABSTRACT

Surgical visualization devices are provided which include a substrate having at least one imaging device and a plurality of fasteners coupled thereto for attaching the substrate to patient tissue. Systems and methods utilizing the surgical visualization devices are also provided.

19 Claims, 5 Drawing Sheets

(56) References Cited

U.S. PATENT DOCUMENTS

| | | | |
|---|---|---|---|
| 8,911,358 B2* | 12/2014 | Koninckx | A61B 1/00181 600/102 |
| 8,961,560 B2* | 2/2015 | Avelar | A61B 17/0469 606/228 |
| 2002/0007110 A1 | 1/2002 | Irion | |
| 2002/0022767 A1 | 2/2002 | Dohi et al. | |
| 2005/0014994 A1 | 1/2005 | Fowler et al. | |
| 2005/0143624 A1 | 6/2005 | Iddan | |
| 2005/0165272 A1* | 7/2005 | Okada | A61B 1/0008 600/114 |
| 2006/0020213 A1 | 1/2006 | Whitman et al. | |
| 2006/0074307 A1 | 4/2006 | Igarashi et al. | |
| 2006/0149135 A1* | 7/2006 | Paz | 600/201 |
| 2008/0139881 A1 | 6/2008 | Cover et al. | |
| 2008/0167546 A1 | 7/2008 | Youmans et al. | |
| 2008/0231963 A1 | 9/2008 | Batchko et al. | |
| 2008/0312500 A1 | 12/2008 | Asada et al. | |
| 2009/0076325 A1 | 3/2009 | Yokoi et al. | |
| 2009/0112236 A1* | 4/2009 | Stopek | A61L 17/12 606/151 |
| 2009/0259102 A1 | 10/2009 | Koninckx et al. | |
| 2009/0299137 A1 | 12/2009 | Gal et al. | |
| 2009/0326321 A1 | 12/2009 | Jacobsen et al. | |
| 2010/0010294 A1 | 1/2010 | Conlon et al. | |
| 2010/0152539 A1* | 6/2010 | Ghabrial et al. | 600/118 |
| 2010/0323961 A1* | 12/2010 | Stopek | 514/7.6 |
| 2011/0118553 A1* | 5/2011 | Stopek | A61B 1/00167 600/245 |
| 2011/0257488 A1* | 10/2011 | Koyama et al. | 600/249 |
| 2011/0264138 A1* | 10/2011 | Avelar | A61B 17/06166 606/228 |
| 2011/0319932 A1* | 12/2011 | Avelar | A61B 17/0469 606/228 |
| 2012/0078236 A1 | 3/2012 | Schoepp | |
| 2012/0296163 A1 | 11/2012 | Stopek | |

FOREIGN PATENT DOCUMENTS

| | | |
|---|---|---|
| EP | 1199037 A2 | 4/2002 |
| EP | 1902663 A1 | 3/2008 |
| EP | 2353537 A1 | 8/2011 |
| EP | 2524664 A1 | 11/2012 |
| WO | 2005082248 A1 | 9/2005 |
| WO | 2009144729 | 12/2009 |

OTHER PUBLICATIONS

European Search Report for corresponding EP12168467 mailing date of Jul. 16, 2012.
Examination Report issued in corresponding AU Patent Application No. 2013201998 dated Mar. 26, 2014.
European Examination Report for EP 12 168 467.4 dated Apr. 29, 2015.
European Search Report issued in corresponding application No. 13161541.1 on Oct. 15, 2015.
Chinese Office Action issued in corresponding application No. 201310108086.5 on Oct. 24, 2016.
Chinese Office Action issued in corresponding application No. 201310108086.5 on Feb. 25, 2016.

* cited by examiner

INTEGRATED SELF-FIXATING VISUALIZATION DEVICES, SYSTEMS AND METHODS

CROSS REFERENCE TO RELATED APPLICATION

The present application claims the benefit of and priority to U.S. Provisional Application Ser. No. 61/617,830, filed on Mar. 30, 2012, the entire contents of which are incorporated herein by reference.

TECHNICAL FIELD

The present disclosure relates to an integrated surgical visualization apparatus, method and system. More specifically, the present disclosure relates to the integration of small cameras and visualization technologies into self-fixation and/or stabilization substrates and surgical devices for providing improved visualization during surgery.

BACKGROUND OF RELATED ART

Endoscopic and laparoscopic minimally invasive procedures have been used for introducing medical devices inside a patient and for viewing portions of the patient's anatomy. Typically, to view a desired anatomical site, a surgeon may insert a rigid or flexible endoscope inside the patient to render images of the anatomical site. In laparoscopic or minimally invasive procedures, visualization technologies are typically centered on the direct integration of the camera component onto the end effector of a surgical instrument, i.e. grasper, clip applier, stapler, and the like, for observing "line of sight" and immediate space in which the respective instrument interrogates tissue. Because the camera is part of the surgical instrument, during a procedure, the surgeon is required to bring the tip of the instrument close to the surgical site, thus eliminating a global view of the surgical site.

The direct integration of the camera component onto the surgical instrument may compromise the ability of the surgeon to manipulate between the camera and the surgical tools when all devices are located along a single axis. In addition, introducing the camera and the surgical tools through working channels of the instrument may compromise its flexibility. Furthermore, during surgical procedures, the surgeon often navigates the instruments through tortuous paths and, thus, the rotational orientation of the instrument may not be aligned with the expected surgical view of the anatomical site. Moreover, the presence of the camera and associated wiring within the instrument takes up space and may interfere with the procedure.

Accordingly, there is a need for an effective, hands free integrated camera/visualization approach which provides a global view of the surgical site.

SUMMARY

The present disclosure provides surgical devices and systems integrating imaging devices with self-fixation and/or stabilization substrates and fibers, i.e. textiles, films, foams, fibers, composite materials, and combinations thereof, for providing improved visualization during surgical procedures and minimize and/or eliminate the need for secondary visualization sources such as scopes. The integrated imaging devices may include a camera and/or illumination source. The substrates may include a means of self-fixation to patient's tissue such as for example, barbs, grips, reactive chemicals or adhesives, fasteners, hooks, and combinations thereof. One or more integrated imaging devices may be rolled and deployable with a delivery tube into patient tissue to provide a global view of the surgical or anatomical site. In one aspect, a self-fixating substrate may include an array of cameras and light sources to illuminate and visualize an entire surgical field.

The present disclosure provides a surgical visualization apparatus including a substrate having a fixating segment having a plurality of fasteners configured to attach the self-fixating substrate to patient tissue; and at least one imaging device coupled to the self-fixating substrate and directed outwardly from the self-fixating substrate such that when the self-fixating substrate is coupled to the tissue, the at least one imaging device is configured to visualize a surgical field.

The present disclosure also provides a surgical visualization apparatus including a fiber having a plurality of barbs configured to attach the fiber to patient tissue; and at least one imaging device coupled to a portion of the fiber and configured to visualize a surgical field.

The present disclosure provides integrated self-fixating visualization systems which include a substrate including a fixating segment having a plurality of fasteners configured to attach the substrate to patient tissue; a plurality of imaging devices coupled to the substrate and directed outwardly from the substrate such that when the substrate is coupled to the tissue, the at least one imaging device is configured to visualize and capture images of a surgical field; and a monitor for displaying the images.

The present disclosure provides methods of providing visualization of an internal surgical site of a patient, including providing a substrate having a fixating segment and having at least one attachment element coupled to the fixating segment and configured to attach the substrate to patient tissue; a plurality of imaging devices coupled to the substrate, wherein the plurality of imaging devices form an array on the substrate for capturing images of an internal site of a patient; attaching the substrate to a predetermined location in the patient's tissue; and visualizing the internal site on a display.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Various embodiments of surgical visualization device, system and methods disclosed herein may be employed in endoscopic, laparoscopic, open surgical procedures, interventional and/or intraluminal procedures such as GI sheathing (metabolic/bariatric) and/or banding, and/or for more advanced minimally invasive procedures such as those which employ a device that facilitates multiple instrument access through a single opening and permits a user to operate through a single entry point, i.e., navel, vagina and/or anus, and combinations thereof, where additional visualization due to compromising space, is required. In addition, the system of the present disclosure may be utilized for post-operative monitoring, diagnostics and combinations thereof.

In embodiments, the integrated self-fixating visualization apparatus, system and methods of the present disclosure may be utilized in lieu of or adjunctive to a traditional scope and/or surgical instrument, and the apparatus may be specifically designed for use with instruments including an endoscope and additional instruments such as graspers, staplers, forceps or the like introduced within a portal member to carry out the surgical procedure, and/or other access devices. An example of such a surgical portal is disclosed in U.S. Patent Application Publication No. 2009/0093752 A1, filed Oct. 2, 2008, the entire contents of which is hereby incorporated by reference.

In embodiments, the device may be used to guide other instruments by sight or electronically to very precise anatomical sites, such as for example tumor and/or disease sites. In embodiments, for example, the apparatus may be utilized for complex thoracic surgeries where the apparatus may be deployed into the chest wall or lung directly for added visualization of critical vessels and/or pulmonary structures. In other embodiments, the integrated self-fixating visualization apparatus may be used to communicate with visualization technology utilized in a surgical instrument, i.e. a laparoscopic instrument, for positioning of the surgical instrument to the target or predetermined anatomical site.

Various embodiments of the integrated self-fixating visualization apparatus of the present disclosure may comprise devices inserted in a patient to provide visualization of the target site. These devices may be introduced into the patient using minimally invasive procedures through natural orifices such as those mentioned above, or via a device inserted through a trocar, for example, and may be adapted to provide images of the surgical site or anatomic location such as the lungs, liver, stomach, gall bladder, urinary tract, reproductive tract, and intestinal tissue, for example. Once positioned at the target site, the surgical visualization devices provide images that enable the surgeon to more accurately diagnose and provide more effective treatment of the diseased tissue. In embodiments, the integrated self-fixating visualization apparatus may be inserted into the tissue treatment region percutaneously. In other embodiments, the integrated surgical visualization device may be introduced into the tissue treatment region endoscopically (e.g., laparoscopically and/or thoracoscopically), through small keyhole incisions via a trocar, or through a natural orifice.

Embodiments of the surgical visualization devices may provide images of the desired tissue during in-vivo treatment procedures used to ablate or destroy live cancerous tissue, tumors, masses, lesions, and other abnormal tissue growths present at the tissue treatment site. In embodiments, the surgical visualization devices may be configured to transmit electrical signals to a receiver and then convert the signals into a viewable image. The signals may be transmitted outside the patient either wirelessly or through electrical conductors placed percutaneously or through the same access path as the translumenal endoscopic access device. Other embodiments of the surgical visualization devices may be powered by on-board power sources, such as a battery, percutaneous electrical conductors, wireless power conductors, or electrical conductors introduced along the same path as the translumenal endoscopic access devices.

In various other embodiments, a variety of surgical visualization end effector devices may be coupled to a suitable applier and introduced through the flexible working channel of an endoscope introduced inside a patient through a natural opening. Suitable examples of such surgical visualization end-effectors include, but are not limited to graspers, clip appliers, staplers, retraction clips, tissue clamps, endoscope stabilizers, electrical power distribution devices, space creators such as devices configured to create space between internal body lumen, organs, and/or dissected sections of tissue, pace makers, vascular access ports, injection ports (such as used with gastric bands), and gastric pacing devices, among other devices.

The Surgical Visualization Apparatus

Figure 1:
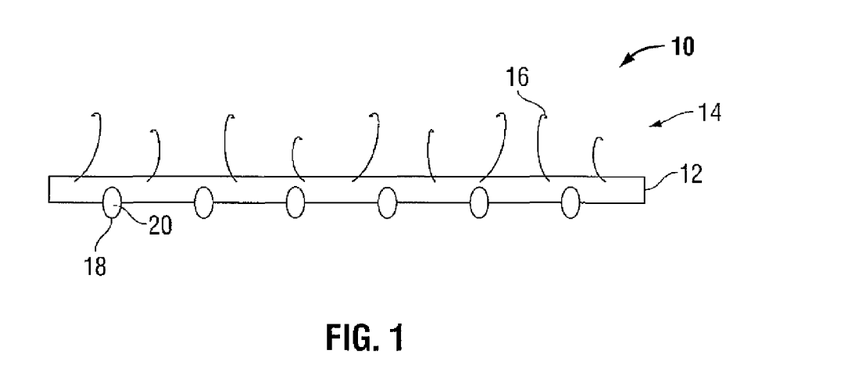
FIG. 1 is a side cross sectional view of a surgical visualization device in accordance with the embodiments of the present disclosure.
Figure 2A:
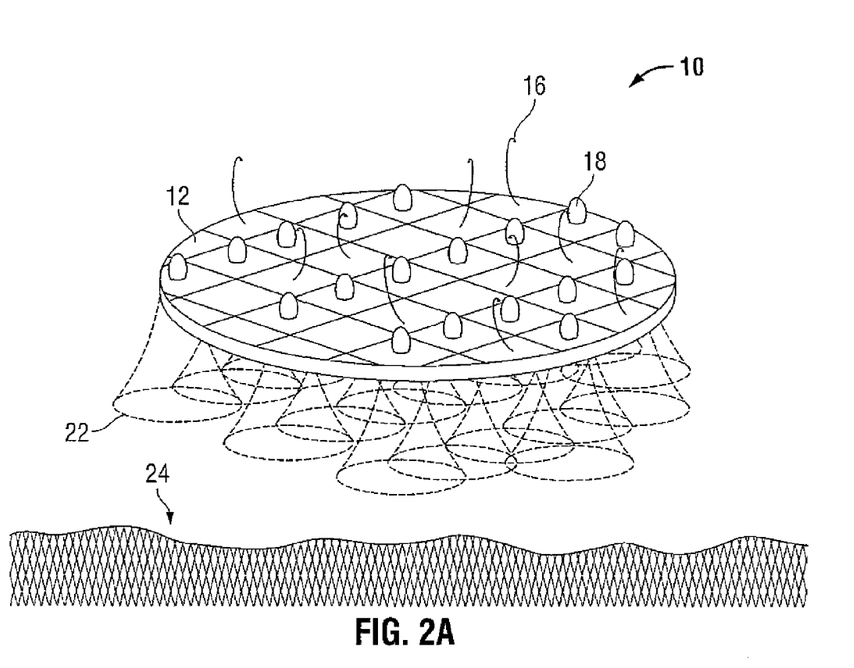
FIG. 2A is a top perspective view of the surgical visualization device in accordance with the embodiments of the present disclosure.

FIG. 1 illustrates an embodiment of a surgical or integrated self-fixating visualization apparatus 10. The surgical visualization apparatus 10 includes a substrate 12 including a fixating segment 14 having a plurality of fasteners 16 configured to attach the substrate 12 to patient tissue and/or organs. The surgical visualization apparatus 10 includes at least one imaging device 18 coupled to the substrate 12. The imaging device 18 may include at least one camera 20 having at least one lens (not shown). The lens may be directed outwardly from the substrate 12 such that when the substrate is attached to patient tissue, the lens may be oriented away from the tissue to capture images of the surgical field or anatomical site 24 (FIG. 2A).

In embodiments, the imaging device 18 may include one or more light or illumination sources (not shown). In other embodiments, the surgical visualization apparatus 10 may also include one or more light or illumination source to illuminate the site to be imaged. In embodiments, illumination may be achieved using a solid state element, such as a light emitting diode (LED) based light source of various wavelength, including those for surgical illumination and/or for detecting disease. In embodiments, the light source may include a single LED or combination LED to provide light of the appropriate spectrum. In embodiments, the LED based light source may be white or fluorescent. Alternative illumination sources may include fluorescent and/or near infrared light with an optical and/or digital filter. In other embodiments, fiber optic light sources may be introduced through the working channel of a flexible endoscope.

In embodiments, the surgical visualization apparatus 10 may be configured to work synergistically with dyes and/or probes that illuminate specific tissue structures such as nerves, vessels, and ureters, organs, diseases such as tumors, chronic inflammatory disease, etc. and/or injuries.

In embodiments, the substrate 12 may include an array of light sources and/or illumination devices. In embodiments, the light source array may be used to photoactive a sealant, adhesive, anti-adhesive, hemostat, and combinations thereof, utilized during a surgical procedure. In embodiments, photoactivation may also include the use of various filters to exert control over intensity or patterns.

Figure 2B:
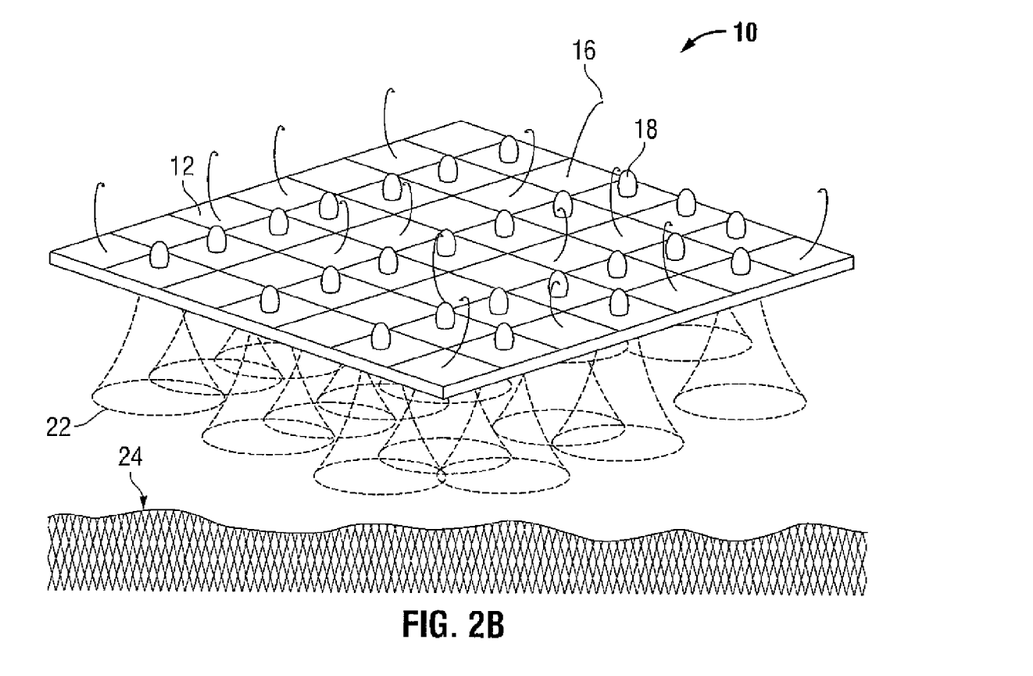
FIG. 2B is a top perspective view of the surgical visualization device in accordance with another embodiment of the present disclosure.
Figure 2C:
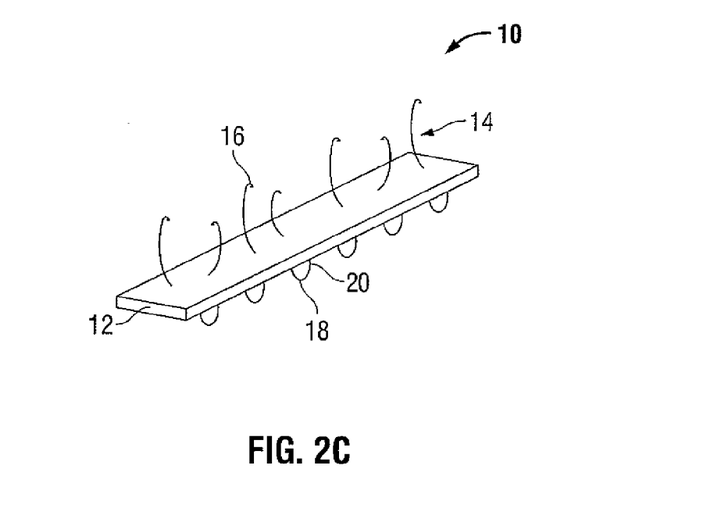
FIG. 2C is a top perspective view of the surgical visualization device in accordance with another embodiment of the present disclosure.

In embodiments, the surgical visualization apparatus 10 may be formed into any geometric shape known in the art such as for example, round, triangular, square, oblique, elliptical, octagonal, rectangular, and diamond. FIGS. 2A-2C illustrate the surgical visualization apparatus 10 in varied shapes such as diamond (FIG. 2A), elliptical (FIG. 2B), and rectangular (FIG. 2C). As illustrated in FIG. 2A, the surgical visualization apparatus 10 may include an array of cameras 20 and/or light sources for capturing images of preferred fields of view 22. The images may then be stitched together to form a single image of an entire surgical field on a monitor display.

In embodiments, the overall length or diameter of the substrate 12 may be from about 1 cm to about 12 cm, in embodiments from about 2 cm to about 10 cm. In embodiments, the diameter of the imaging device 18 may be from about 2 mm to about 8 mm, in embodiments from about 3 mm to about 5 mm.

In embodiments, the lens may be rotated about its optical axis, translated forward and rearward, and may be rotated about a pivot point defined by a tissue keyhole site to control its orientation and obtain a quality image at a desired viewing angle. In embodiments, the lens may be gyrated to provide preferred views. In addition, the lens may be used to pan and/or zoom the images while the surgeon manipulates other surgical instruments to the surgical site.

In embodiments, the lens may be optically coupled to one or more image sensors (not shown) to convert an optical image to an electric signal, similar to that employed in digital cameras and other electronic imaging devices.

In one embodiment, the image sensor may include one or more arrays of charge coupled devices (CCD), charge injection devices (CID) and/or complementary metal oxide semiconductor (CMOS) devices such as active-pixel sensors. The image sensor may capture light and convert it into electrical signals. In one embodiment, the image sensor may include a sensor array with an image input area of approximately 2 mm diameter.

In embodiments, the image sensor may be connected to a circuit board (not shown) including any necessary electronic components or elements for processing, storing, and/or transmitting the images received by the image sensor. The images may be processed by any suitable digital or analog signal processing circuits and/or techniques. Furthermore, the images may be stored in electronic storage media such as, for example, memory devices. In embodiments, the images may be transmitted over a wire or wirelessly to external devices for displaying or further processing the images in real-time. A second circuit board (not shown) may be employed to receive and attach a battery and is coupled to the first circuit board by a connector (not shown).

In embodiments, the imaging device 18 may include a wireless component for wirelessly transmitting images outside the patient and may include a battery (not shown) to operate various electrical and/or electromechanical elements of the camera 20. For example, the battery may supply electrical energy to power light sources, image sensor arrays, and motors for orienting, panning, and zooming the image sensor arrays or the associated optics or lenses. In embodiments, the wireless component may be a radio frequency (RF) device suitable for transmitting images remotely from the patient to an external monitor. In one embodiment, the wireless component may include a wireless transceiver (e.g., RF transmitter and receiver) module. Images received by the image sensor may be wirelessly transmitted/received between the wireless RF device using any well known RF telemetry techniques so as to eliminate the need for hard wired electrical connections.

Figure 3A:
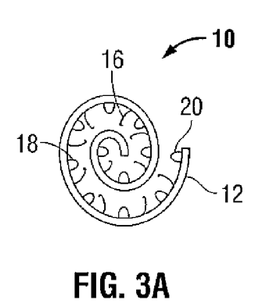
FIG. 3A is an end view of the surgical visualization device in a rolled configuration in accordance with embodiments of the present disclosure.
Figure 3B:
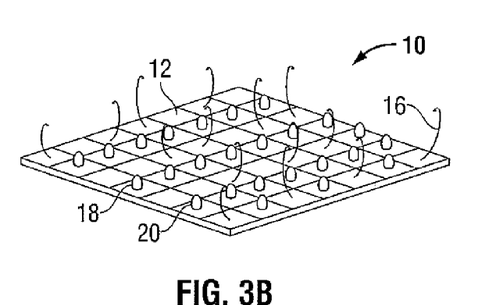
FIG. 3B is a top perspective view of the surgical visualization device in an unrolled configuration in accordance with embodiments of the present disclosure.

In embodiments, the surgical visualization device 10 may be introduced into the patient by compressing or rolling the substrate 12 into a delivery tube (not shown) and deploying the substrate 12 in a predetermined location of a patient. FIGS. 3A and 3B illustrate the surgical visualization device 10 in a rolled or compressed configuration which then may be unrolled when attached to patient tissue.

In embodiments, a single or plurality of integrated self-fixating visualization apparatus 10 may be deployed into tissue or anatomical location such that images and/or videos from each camera may be stitched together to provide a global view of the surgical field. In embodiments, the images provided of the surgical site may be 2-dimensional, 3-dimensional, wide angle, and combinations thereof.

In embodiments, an optical image of the surgical site 410 (FIG. 7) may be formed on the image sensors through the optical lens system of the camera 20. Image signals into which image sensors (i.e., a CCD image sensor) convert the optical image formed thereon are processed in an image signal processor (not shown) and then sent to the image signal processing unit 480 from a transmitter (not shown) through an antenna 460.

Figure 7:
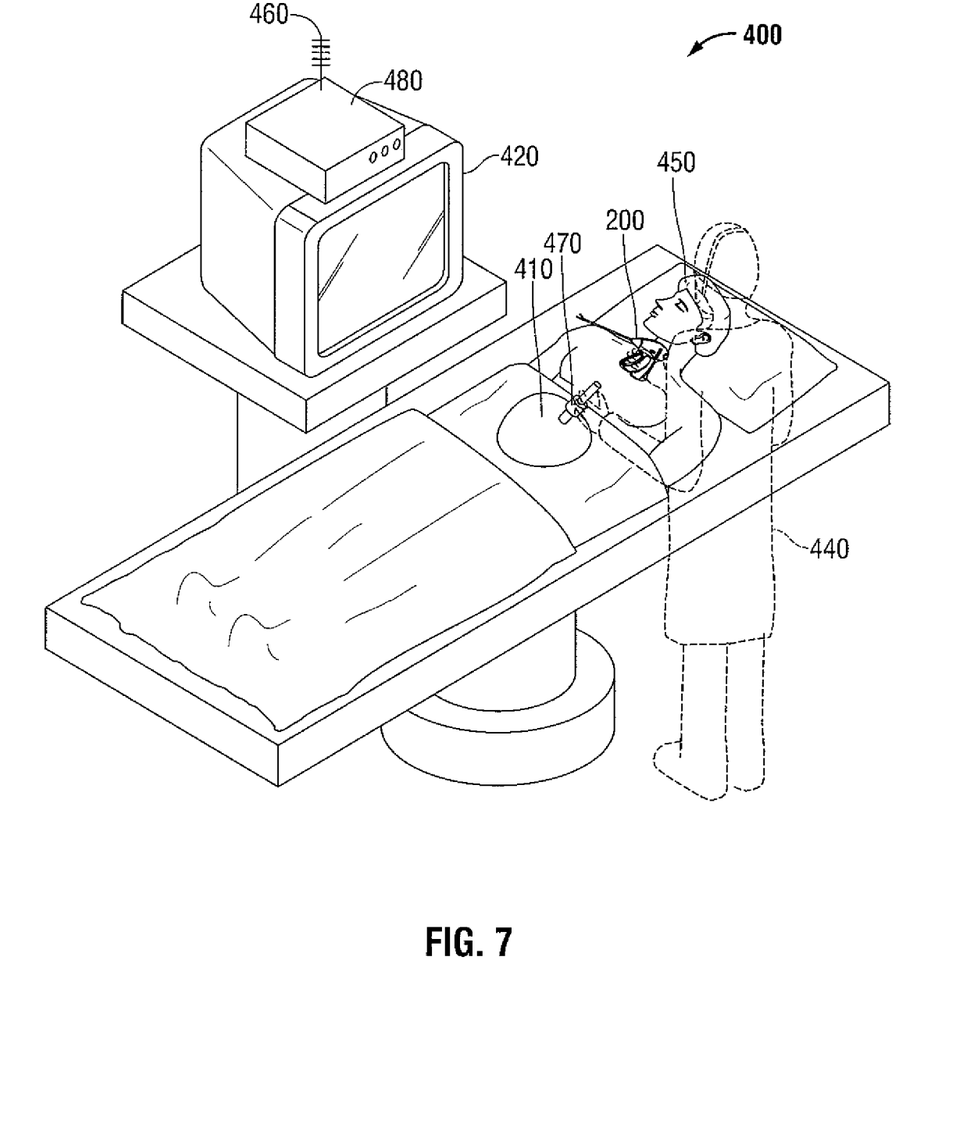
FIG. 7 illustrates a surgical visualization system in accordance with an embodiment of the present disclosure.

In embodiments, the images and/or videos are viewable on a display or monitor 420 as illustrated in the schematic drawing of an integrated, self-fixating visualization system of FIG. 7.

In embodiments, the imaging device 18 may be coupled to the substrate 12 utilizing any methods known in the art such as, for example, hooks or adhesives.

The substrate may be formed of any biocompatible material. The biocompatible substrates are often planar in configuration, however, any two-dimensional or three dimensional shapes suitable for implantation may be used. Some examples of suitable biocompatible substrates include films, foams, meshes, buttresses, patches, tapes, pledgets, occlusion devices, and the like.

Figure 4A:
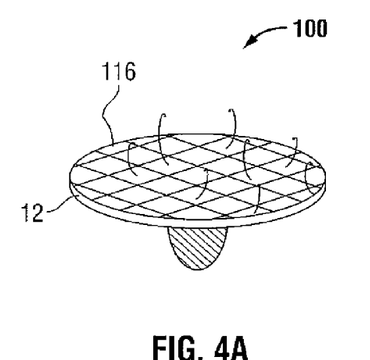
FIG. 4A is a top perspective view of the surgical visualization device in accordance with the embodiments of the present disclosure.
Figure 4B:
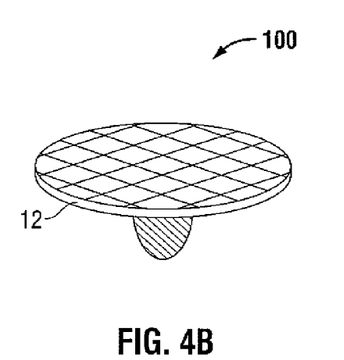
FIG. 4B is a top perspective view of the surgical visualization device in accordance with another embodiment of the present disclosure.

In embodiments, the fasteners 16 may be tacks, darts, anchors, anchors, barbs, grips, hooks and combinations thereof. As shown in FIG. 4a, barbs and/or grips 116 may be utilized to attach the substrate 12 to patient tissue. In alternative embodiments, adhesive 216 may be utilized to attach the substrate 12 to patient tissue.

Figure 5:
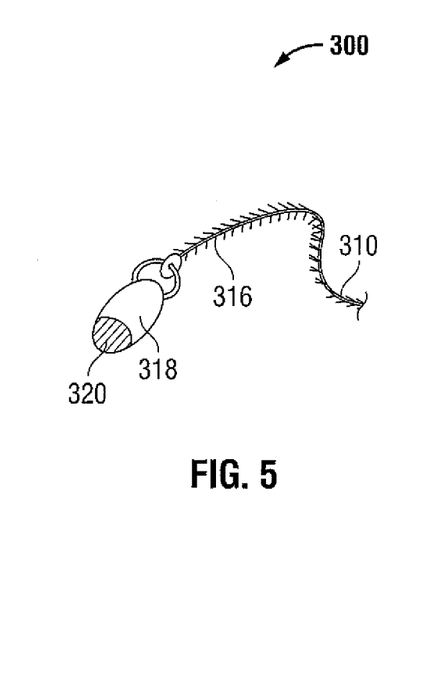
FIG. 5 depicts a perspective view of a fiber including surgical visualization devices in accordance with embodiments of the present disclosure.

As shown in FIG. 5, in embodiments, a surgical visualization apparatus 300 may include a fiber 310 including a plurality of fasteners or barbs 316 configured to attach the fiber to patient tissue. Surgical visualization apparatus 300 may include at least one imaging device 318 coupled to a portion of the fiber 310 and configured to visualize a surgical field. In embodiments, the fiber 300 is a surgical suture. Although shown as a monofilament thread, it is envisioned that fiber 300 may be formed from braided threads, multifilament threads and the like. The cross-sectional geometry of the suture may be of any suitable shape.

Figure 6:
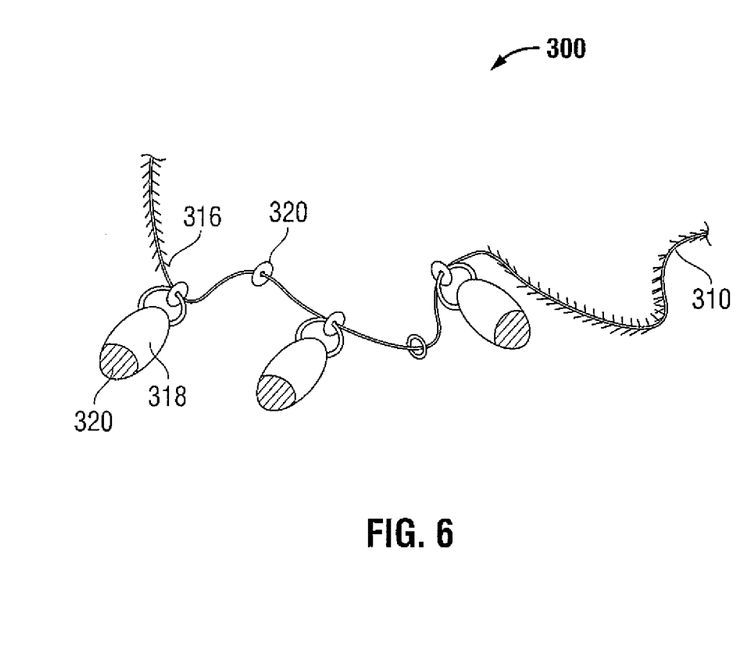
FIG. 6 depicts a perspective view of a fiber including surgical visualization devices in accordance with alternative embodiments of the present disclosure.

In embodiments, the at least one imaging device may include a light source (not shown), a camera 320, and combinations thereof. As illustrated in FIG. 6, in embodiments, the fiber 300 may include an array of imaging devices 318, such as for example cameras 320 and light sources 322. In embodiments, the fiber 300 may be single directional (FIG. 5) or bi-directional (FIG. 6).

In embodiments, the imaging device 318 may be coupled to the fiber 300 utilizing any methods known in the art such as for example, via a loop formed at the end of or at predetermined locations along the fiber 300.

Fiber 300 may include a plurality of barbs 316 formed along a length thereof. Barbs 316 are radially and longitudinally spaced along fiber 300 and may be formed using any suitable method. Barbs 316 on fiber 300 may extend in the same direction along the entire length thereof, or may instead extend in one direction on a first half of fiber 300 and may extend in an opposite direction on a second half of fiber 300. Proximal end or distal end of fiber 300 may include a sharpened tip or needle (not shown) configured for penetrating tissue. The needle may be any surgical needle as are known to those of skill in the art. In embodiments, the needle may be a straight needle. Either or both ends of fiber 300 may include a fixation device (not shown). Non-limiting examples of suitable fixation devices may include surgical pins, screws, suture anchors, nails, and the like.

Barbed fiber 300 may be formed using any technique within the purview of those skilled in the art, such as, for example, extrusion, molding and/or solvent casting. In some embodiments, suture 300 may include a yarn made of more than one filament, which may contain multiple filaments of the same or different materials. Where suture 300 is made of multiple filaments, suture 300 may be made using any known technique such as, for example, braiding, weaving or knitting. Filaments may also be combined to produce a non-woven suture. Suture 300 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

In embodiments, barbs 316 may be formed by making acute angular cuts directly into the suture body, with cut portions pushed outwardly and separated from the body of the suture. The depth of the barbs thus formed in the suture body may depend on the diameter of the material and the depth of the cut.

It is envisioned that the fasteners 16 and/or barbs 316 may be formed of various configurations. Fasteners 16 and/or barbs 316 may be arranged in any suitable pattern, for example, helical, linear, or randomly spaced. The pattern may be symmetrical or asymmetrical. The number, configuration, spacing and surface area of fasteners 16 and/or barbs 316 may vary depending upon the tissue in which the fiber is used, as well as the composition and geometry of the material utilized to form the fiber 300. Additionally, the proportions of fasteners 16 and/or barbs 316 may remain relatively constant while the overall length of fasteners 16 and/or barbs 316 and the spacing of fasteners 16 and/or barbs 316 may be determined by the tissue and/or organ that the substrate and/or fiber is being affixed to. For example, if fiber 300 is to be used on the thoracic cavity wall, fasteners 16 and/or barbs 316 may be made relatively short and more rigid to facilitate entry into this rather firm tissue. Alternatively, if fiber 300 is intended for use in fatty tissue, which is relatively soft, fasteners 16 and/or barbs 316 may be made longer and spaced further apart to increase the ability of the fiber 300 to grip the soft tissue.

The surface area of fasteners 16 and/or barbs 316 may also vary. For example, fuller-tipped fasteners may be made of varying sizes designed for specific surgical applications. For joining fat and relatively soft tissues, larger fasteners may be desired, whereas smaller fasteners may be more suitable for collagen-dense tissues. In some embodiments, a combination of large and small fasteners within the same structure may be beneficial, for example, when a suture is used in tissue repair with differing layer structures. The use of the combination of large and small fasteners with the same suture wherein the fastener sizes are customized for each tissue layer maximizes anchoring properties. In particular embodiments, a single directional suture may have both large and small fasteners; in other embodiments a bi-directional suture may have both large and small fasteners. The fasteners formed may include geometrical shapes such as round, triangular, square, oblique, elliptical, octagonal, rectangular, and flat.

As mentioned above, the substrate 12 described herein may be formed from any biocompatible material. In embodiments, the imaging device 18 may utilize materials which are absorbable, degradable or corrosion sensitive such that the residual mass remaining following some critical implantation time is negligible. In embodiments, the camera 20, 320 may be composed of known bioabsorbable glasses, ceramics, polymers, and metals such that it is completely resorbable.

For example, the device and camera may be made from natural, synthetic, bioabsorbable or non-bioabsorbable materials. It should of course be understood that any combination of natural, synthetic, bioabsorbable and non-bioabsorbable materials may be used to form the devices and camera components described herein. The term "bioabsorbable" as used herein is defined to include both biodegradable and bioresorbable materials. By bioabsorbable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural bioabsorbable materials include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers. Examples of bioabsorbable silk-based circuits and optics can be found in "Silicon Electronics on Silk as a Path to Bioresorbable, Implantable Devices," Applied Physics Letters 95, 133701 (2009), and "Bioactive Silk Protein Biomaterial Systems for Optical Devices," Biomacromolecules, 9 (4), 1214-1220, 2008

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic bioabsorbable polymers include polyhydroxy acids prepared from lactone monomers, such as glycolide, lactide, caprolactone, $\epsilon$-caprolactone, valerolactone, and $\delta$-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly (hydroxyvaleric acid); poly(lactide-co-($\epsilon$-caprolactone-)); poly(glycolide-co-$\epsilon$-caprolactone)); polycarbonates; poly(pseudo amino acids); poly(amino acids); poly(hydroxyalkanoate)s, including polyhydroxybutyrate, polyhydroxyvalerate, poly(3-hyydroxybutyrate-co-3-hydroxyvalerate), polyhydroxyoctanoate, and polyhydroxyhexanoate; polyalkylene oxalates; polyoxaesters; polyanhydrides; polyortho esters; and copolymers, block copolymers, homopolymers, blends, and combinations thereof.

In certain embodiments, the biocompatible devices may be formed using a combination of bioabsorbable and non-bioabsorbable polymers.

Some non-limiting examples of suitable non-bioabsorbable materials include polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, including expanded polytetrafluoroethylene (ePTFE) and condensed polytetrafluoroethylene c(PTFE), fluoropropylenes, fluoroPEGSs, and polytetrafluoroethylene; polyamides, including Nylon 6, Nylon 6,6, Nylon 6,10, Nylon 11, and Nylon 12; polycaprolactam; polyamines; polyimines; polyesters, such as polyethylene terephthalate, polyethylene naphthalate, polytrimethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The biocompatible substrates and/or fibers of the present disclosure may be formed using any method within the purview of those skilled in the art. Some non-limiting examples include, weaving, knitting, braiding, crocheting, extruding, spraying, casting, molding, laminating, lyophilization, freeze-drying, and combinations thereof. In some embodiments, the biocompatible substrate may be a two or three dimensional surgical mesh which is woven, knitted, braided, or crocheted from at least one first filament to form the substrate. In certain embodiments, the biocompatible substrate may be a surgical mesh consisting of at least one first filament made of polyethylene terephthalate.

The Method

In embodiments, methods of providing visualization of an internal surgical site of a patient of the present disclosure include the step of providing a substrate or fiber having a fixating segment and including at least one attachment element coupled to the fixating segment and at least one imaging device coupled to the substrate or fiber for capturing images of an internal site of a patient. In embodiments, the fixating segment may include a plurality of imaging devices which form an array on the substrate for capturing images of an internal site of a patient. In embodiments, the method includes attaching the substrate and/or fiber to a predetermined location in the patient's tissue. In embodiments, the method includes attaching a plurality of substrates and/or fibers to an anatomical site.

In embodiments, the attaching step includes compressing the substrate into a tube and deploying the substrate in a predetermined internal location of a patient as described in detail above. In alternative embodiments, the attaching step may include attaching and/or deploying the substrate to a predetermined location or locations in the patient tissue utilizing any suitable delivery device. In other embodiments, the fiber may be attached to patient tissue or organs via barbs which provide a counter force in the tissue so that the fiber remains in the tissue.

In embodiments, as illustrated in FIG. 7, surgeon 440 has deployed the surgical visualization apparatus 10 into patient's 450 surgical site 410 with a delivery device 200. The surgeon 440 may then perform the predetermined procedure with the appropriate surgical instrument 470. As mentioned above, images that are captured via the surgical visualization apparatus 10 may be displayed on monitor 420.

In embodiments, a single or series of surgical visualization devices may be deployed or attached in any tissue or anatomical location where the delivery device can access. A plurality of surgical visualization devices may be deployed in predetermined spaced apart locations of patient tissue such that a field of view of each adjacent camera overlaps a field of view of the adjacent camera. In embodiments, images and/or videos from each camera may be processed or "stitched" together to provide a global view of the surgical field and/or a single image on a display.

In embodiments, the method may include illuminating the target area with a light source as described in detail above.

In addition, once attached to patient tissue, the surgical visualization device may help guide and position a surgical instrument to a predetermined anatomical site via camera to camera communication either with the camera on the surgical instrument or with an adjacent surgical visualization apparatus.

In embodiments, the surgical visualization apparatus may be configured and dimensioned such that the imaging device is removable following use utilizing the same deployment methods or any alternative secondary retrieval instrument. In embodiments, the imaging device may be removed by any means known in the art such as mechanical, magnetic, and/or chemical means.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical visualization apparatus, comprising:
 a planar, non-conductive mesh substrate having a plurality of hooks on a first side thereof and configured to attach the planar, non-conductive mesh substrate to patient tissue; and
 a plurality of cameras coupled to non-conductive portions of a second side of the planar, non-conductive mesh substrate, the plurality of cameras forming an array with predetermined spacing on the planar, non-conductive mesh substrate such that when the planar, non-conductive mesh substrate is coupled to patient tissue, the plurality of cameras is configured to visualize an entire surgical field as a single image, the single image formed from a plurality of images having overlapping fields of view and which are stitched together from the plurality of cameras by a processor.

2. The surgical visualization apparatus according to claim 1, wherein the planar, non-conductive mesh substrate further includes a light source, the light source including light emitting diodes.

3. The surgical visualization apparatus according to claim 1, wherein the planar, non-conductive mesh substrate is bioabsorbable.

4. The surgical visualization apparatus according to claim 1, wherein at least a portion of one camera of the plurality of cameras is absorbable.

5. The surgical visualization apparatus according to claim 1, wherein at least a portion of one camera of the plurality of cameras is rotatable relative to the planar, non-conductive mesh substrate for capturing images of a target site to provide preferred fields of view.

6. The surgical visualization apparatus according to claim 5, wherein the single image is viewable on a display.

7. The surgical visualization apparatus according to claim 1, wherein the planar, non-conductive mesh substrate is deformable such that the planar, non-conductive mesh substrate is adapted to be deployable from a tube into a target site.

8. An integrated self-fixating visualization system, comprising:
 a threaded suture substrate including at least one fixating segment having a plurality of fasteners on a first side thereof and configured to attach the threaded suture substrate to patient tissue; and
 a plurality of imaging devices coupled directly to the threaded suture substrate on a second side thereof, each imaging device of the plurality of imaging devices coupled to the threaded suture substrate via a loop formed at an end of or at a predetermined location along the threaded suture substrate such that when the threaded suture substrate is coupled to patient tissue, the plurality of imaging devices is configured to visualize a single image of an entire surgical field from a plurality of images having overlapping fields of view and which are stitched together to form the single image by a processor.

9. The integrated self-fixating visualization system according to claim 8, wherein at least one imaging device of the plurality of imaging devices is a camera.

10. The integrated self-fixating visualization system according to claim 8, wherein at least a portion of one imaging device of the plurality of imaging devices is absorbable.

11. The integrated self-fixating visualization system according to claim 8, wherein one imaging device of the plurality of imaging devices includes a material selected from the group consisting of glasses, ceramics, polymers, metals, and combinations thereof.

12. The integrated self-fixating visualization system according to claim 8, wherein one imaging device of the plurality of imaging devices uses wireless transmission.

13. The integrated self-fixating visualization system according to claim 8, wherein at least one portion of one imaging device of the plurality of imaging devices is rotatable to provide preferred fields of view.

14. The integrated self-fixating visualization system according to claim 8, wherein at least one imaging device of the plurality of imaging devices is configured to communicate with another imaging device of the plurality of imaging devices for positioning a surgical instrument at a predetermined anatomical site.

15. The integrated self-fixating visualization system according to claim 8, wherein the threaded suture substrate is formed from monofilament threads, multifilament threads, braided threads, and combinations thereof.

16. The integrated self-fixating visualization system according to claim 8, wherein the at least one fixating segment includes a plurality of barbs formed along a length thereof.

17. The integrated self-fixating visualization system according to claim 16, wherein the plurality of barbs extend in the same direction along an entire length of the threaded suture substrate.

18. The integrated self-fixating visualization system according to claim 16, wherein the plurality of barbs extend in one direction on a first half of the threaded suture substrate and extend in an opposite direction on a second half of the threaded suture substrate.

19. The integrated self-fixating visualization system according to claim 8, wherein the plurality of imaging devices form an array with predetermined spacing on the threaded suture substrate for capturing the plurality of images.

* * * * *